United States Patent
Stanchina et al.

(10) Patent No.: US 9,778,111 B2
(45) Date of Patent: Oct. 3, 2017

(54) METHOD FOR ESTIMATING A CARDIAC FREQUENCY AND ASSOCIATED DEVICE

(71) Applicant: Commissariat a l'energie atomique et aux energies alternatives, Paris (FR)

(72) Inventors: Sylvain Stanchina, Grenoble (FR); Anne Koenig, Saint Martin d'Uriage (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/445,021

(22) Filed: Feb. 28, 2017

(65) Prior Publication Data

US 2017/0248469 A1    Aug. 31, 2017

(30) Foreign Application Priority Data

Feb. 29, 2016 (FR) ...................... 16 51656

(51) Int. Cl.

| | |
|---|---|
| G01J 3/00 | (2006.01) |
| G01J 3/427 | (2006.01) |
| G01N 21/359 | (2014.01) |
| G01N 21/49 | (2006.01) |
| G01N 21/59 | (2006.01) |
| A61B 5/024 | (2006.01) |
| G01N 21/31 | (2006.01) |

(52) U.S. Cl.
CPC .............. *G01J 3/427* (2013.01); *A61B 5/024* (2013.01); *G01N 21/359* (2013.01); *G01N 21/49* (2013.01); *G01N 21/59* (2013.01); *G01N 2021/3129* (2013.01)

(58) Field of Classification Search
CPC .......... G01J 3/42; G01J 3/427; G01N 21/359; G01N 21/49; G01N 21/59; A61B 5/024
See application file for complete search history.

(56) References Cited

U.S. PATENT DOCUMENTS

| | | | |
|---|---|---|---|
| 2009/0105565 A1* | 4/2009 | Xu | ..................... A61B 5/14532 600/310 |
| 2013/0072771 A1 | 3/2013 | Gu et al. | |
| 2015/0196257 A1 | 7/2015 | Yousefi et al. | |

OTHER PUBLICATIONS

French Preliminary Search Report issued Nov. 28, 2016 (with Written Opinion) in French Application 16 51656 filed on Feb. 29, 2016 (with English Translation of Categories of Cited Documents).

* cited by examiner

*Primary Examiner* — Abdullahi Nur
(74) *Attorney, Agent, or Firm* — Oblon, McClelland, Maier & Neustadt, L.L.P.

(57) ABSTRACT

The invention is a method for estimating a cardiac frequency via the detection of radiation backscattered or transmitted by a bodily zone. The part is illuminated, simultaneously or successively, by light radiation extending over a first spectral band and a second spectral band. A photodetector detects radiation emitted by the bodily zone under the effect of its illumination, in each of the spectral bands. A first detection function and a second detection function are formed from the radiation detected in each spectral band, respectively. The method allows the cardiac frequency to be determined via the determination of characteristic instants that are identified from the first detection function and the second detection function simultaneously.

11 Claims, 5 Drawing Sheets

METHOD FOR ESTIMATING A CARDIAC FREQUENCY AND ASSOCIATED DEVICE

FIELD OF THE INVENTION

The technical field of the invention is the optical measurement of a cardiac frequency of an individual or of an animal.

BACKGROUND

Optical measurements are frequently implemented to determine physiological parameters of a living being, in particular blood-related parameters. Devices, called pulse oximeters, are commonly used to determine an oxygen saturation of the haemoglobin in the blood. These measurements are based on the absorption of light by the haemoglobin, the latter varying between oxyhaemoglobin and deoxyhaemoglobin. Commercial devices are widely used, these devices being based on a measurement of the light transmitted by a sufficiently thin member, in an infrared spectral band and in a red spectral band. The examined member may in particular be the end of a finger or the lobe of an ear. Measurements of the transmitted light, in each of the spectral bands, allow concentrations of oxyhaemoglobin and deoxyhaemoglobin in the blood to be estimated, from which the oxygen saturation of the blood is estimated. These measurements also allow a pulsatile blood flow to be detected and a cardiac frequency to be deduced therefrom. Most commercial oximeters also allow the cardiac frequency to be estimated from measurements carried out in one or other spectral band.

European patent EP2355693 for example describes a device including a first light source emitting at a red wavelength and a second light source emitting at an infrared wavelength. A photodetector is configured to detect light radiation emanating from a finger illuminated by one of the light sources. The infrared light source is in particular used to detect the presence of the finger against the device, subsequent to which the red light source is activated, so as to allow parameters such as cardiac frequency or pulse oximetry to be determined.

U.S. Pat. No. 9,042,971 describes a portable actigraphy device allowing a cardiac frequency to be determined optically via detection of light radiation backscattered by a finger under the effect of an illumination. This device allows measurements to be carried out in a back-scatter configuration, also called the reflectance configuration, the light sources being placed adjacent to the photodetector.

The inventors have observed that such devices may make errors when measuring cardiac frequency, in particular when they are worn by a moving person. The invention proposes to solve this problem, and hence allow more reliable measurements of cardiac frequency to be obtained.

SUMMARY

A first subject of the invention is a method for estimating a cardiac frequency of a living being comprising the following steps:
  a) illuminating a bodily zone of the living being with an incident light beam in a first spectral band;
  b) detecting light radiation transmitted or backscattered, in the first spectral band, by the bodily zone under the effect of the illumination;
  c) determining a first detection function, representing a variation as a function of time of an intensity of the light radiation thus detected;
  d) identifying characteristic instants from the first detection function, and calculating an occurrence frequency of the characteristic instants;
  e) estimating a cardiac frequency from the occurrence frequency;
wherein:
  steps a) to b) are also implemented in a second spectral band, such that step c) includes determining a second detection function representing a variation as a function of time of an intensity of the light radiation detected in the second spectral band;
  step d) includes identifying characteristic instants from the second detection function and selecting characteristic instants, identified from each detection function, and appearing in temporal coincidence, the occurrence frequency being calculated from the characteristic instants thus selected.

By temporal coincidence, what is meant is simultaneously, i.e. in the same time window. This time window may be preset or adjustable.

By light beam or light radiation, what is meant is a flux of photons the spectral band of which is comprised in the visible domain, or in the near infrared domain, or in the near UV domain, for example between 200 nm and 1000 nm.

The cardiac frequency may be equal to the occurrence frequency.

The second spectral band is preferably different from the first spectral band.

According to an embodiment, step d) includes calculating a first derived function, derived from the first detection function, and a second derived function, derived from the second detection function, and identifying characteristic instants from each of the derived functions.

According to an embodiment, each derived function is obtained via a difference between the value of a corresponding detection function at two different instants.

The method may include one of the following features, individually or in combination:
  the first spectral band includes wavelengths comprised between 600 and 700 nm;
  the second spectral band includes wavelengths comprised between 750 nm and 1 µm;
  the first spectral band extends between 600 nm and 700 nm, and/or the second spectral band extends between 750 nm and 1 µm, and preferably between 810 nm and 1000 nm;
  the first spectral band extends, mainly or entirely, below 805 nm, whereas the second spectral band extends, mainly or entirely, above 805 nm.
  the detected radiation is radiation backscattered by the bodily zone under the effect of its illumination.

The detected radiation may be backscattered radiation, in which case the light source and the photodetector are placed adjacent one with respect to the other. The detected radiation may also be transmitted radiation, in which case the bodily zone extends between the light source and the photodetector.

Preferably, the first spectral band and the second spectral band do not overlap, or if they do, only by a negligible amount.

Another subject of the invention is a device including:
  a light source able to emit an incident light beam that propagates towards a bodily zone of the living being, in a first spectral band and in a second spectral band;

a photodetector, configured to detect, in the first spectral band and in the second spectral band, radiation backscattered or transmitted by the bodily zone under the effect of its illumination by the incident light beam;

a processor, configured to implement steps c) to e) of the method described herein from the radiations detected by the photodetector.

The photodetector may be configured to detect radiation backscattered by the bodily zone under the effect of its illumination. Alternatively, the photodetector is configured to detect radiation transmitted by the illuminated bodily zone.

The light source may include:

a first elementary light source, configured to emit a first incident light beam in the first spectral band;

a second elementary light source, configured to emit a second incident light beam in the second spectral band.

Other advantages and features will become more clearly apparent from the following description of particular embodiments of the invention, which are given by way of nonlimiting example and shown in the appended figures, which are listed below.

BRIEF DESCRIPTION OF THE DRAWINGS

FIGS. 6A to 6D were obtained by implementing the method in a back-scatter configuration.

DETAILED DESCRIPTION OF THE ILLUSTRATED EMBODIMENTS

Figure 1A:
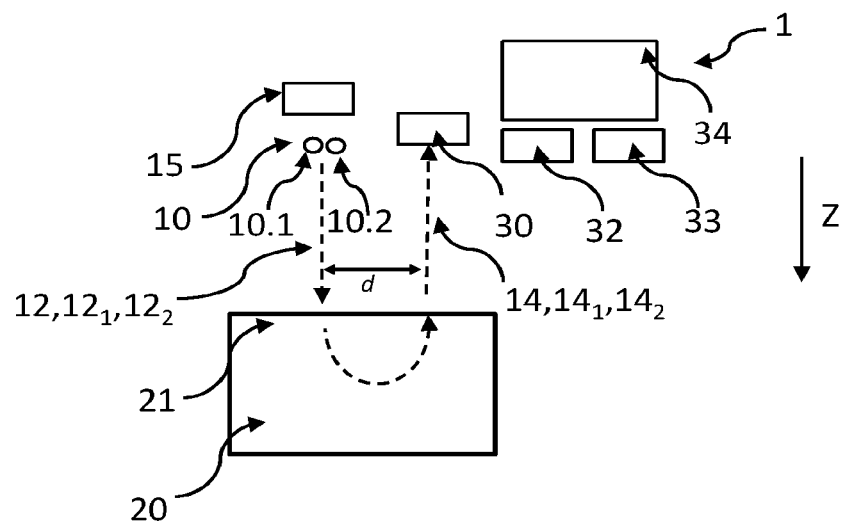
FIGS. 1A and 1B show a first and a second example of a device configured to implement the invention, respectively.

FIG. 1A shows an example of a device 1 allowing the invention to be implemented. A light source 10 emits an incident light beam 12 that propagates towards a sample 20, along a propagation axis Z. The term sample designates a bodily zone of a living being, the cardiac frequency of which it is desired to acquire.

The photons composing the incident light beam 12 penetrate into the sample and some thereof are backscattered in a direction parallel to the propagation axis, in a direction opposite to the latter. These backscattered photons form backscattered radiation 14. The backscattered radiation 14 may be detected by a photodetector 30 placed facing the surface 21 of the sample. The photodetector may be configured so as to detect backscattered radiation emanating from the sample at a distance d, called the back-scatter distance, which is generally non-zero, smaller than a few millimeters and typically smaller than 15 mm or 10 mm.

In this example, the light source 10 includes two elementary light sources $10_1$ and $10_2$. The first elementary light source $10_1$ is a light-emitting diode emitting in a first spectral band $\Delta\lambda_1$ centred on a first wavelength $\lambda_1$ equal to 660 nm. It is a light-emitting diode sold by the manufacturer Kingbright under the reference APT1608SURCK. The second elementary light source $10_2$ is a light-emitting diode emitting in a second spectral band $\Delta\lambda_2$ centred on a second wavelength $\lambda_2$ equal to 940 nm. It is a light-emitting diode sold by the manufacturer Kingbright under the reference APT1608F3C. Thus, the first spectral band $\Delta\lambda_1$ preferably extends between 600 and 700 nm, this covering the red visible spectral band, whereas the second spectral band $\Delta\lambda_2$ preferably extends between 700 and 1000 nm, and more preferably between 810 nm-1000 nm, this corresponding to a spectral band in the near infrared. Preferably, the first spectral band $\Delta\lambda_1$ and the second spectral band $\Delta\lambda_2$ are different and do not overlap. By do not overlap, what is meant is that most of the emission spectrum, and preferably 80% or even more than 90% of the emitted intensity, is not located in the same spectral range.

A microcontroller 15 commands the sequential activation of the elementary light sources $10_1$ and $10_2$. Thus, the sample is successively illuminated by a first incident light beam $12_1$, in the first spectral band $\Delta\lambda_1$, and by a second incident light beam $12_2$, in the second spectral band $\Delta\lambda_2$.

A photodetector 30 detects first backscattered radiation $14_1$, in the first spectral band $\Delta\lambda_1$, under the effect of the illumination by the first incident light beam $12_1$, and second backscattered radiation $14_2$, in the second spectral band $\Delta\lambda_2$ under the effect of the illumination by the second incident light beam $12_2$. In the example shown, the photodetector is a photodiode sold by VISHAY under the reference BPW345, the spectral band of detection of which allows the first and second backscattered radiation to be detected. The back-scatter distance d is, in this example, 7 mm.

A processor 32 is configured to establish a detection function, corresponding to a variation as a function of time of the intensity of radiation detected by the photodetector, in each of the spectral bands. It may be connected to a memory 33 configured to store instructions allowing a method described in this description to be implemented. It may also be connected to a display unit 34.

Figure 1B:
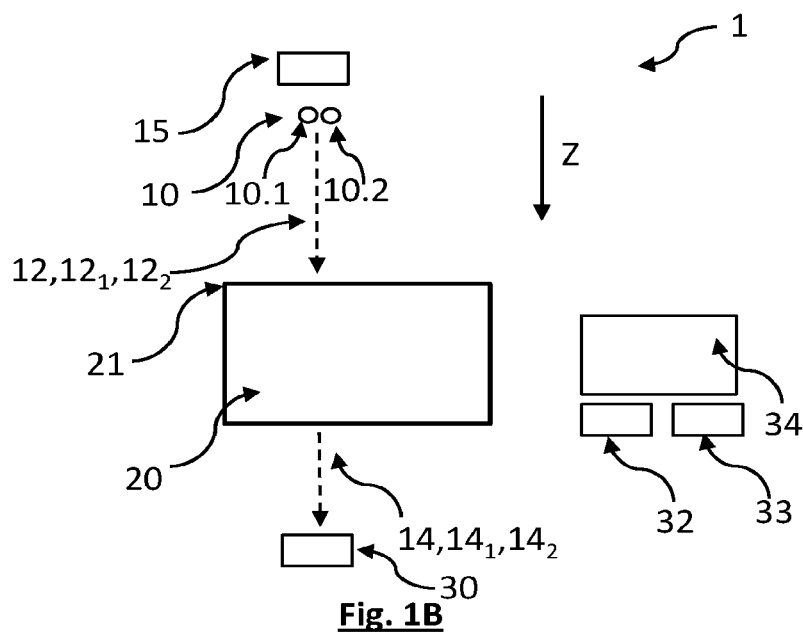

According to another embodiment, which is shown in FIG. 1B, the device 1 is placed in what is called a transmission configuration. In such a configuration, the sample 20 extends between the light source 10 and the photodetector 30. The latter is then configured to detect radiation 14 transmitted by the sample along the propagation axis Z. However, such a device is less compact than the back-scatter device described with reference to FIG. 1A. In addition, a back-scatter device, such as shown in FIG. 1A, is more versatile than a device operating in transmission. Specifically, its operation is independent of the thickness of the analysed bodily zone. It may therefore be placed against various bodily zones, for example a wrist, a finger, or a leg.

Figure 2A:
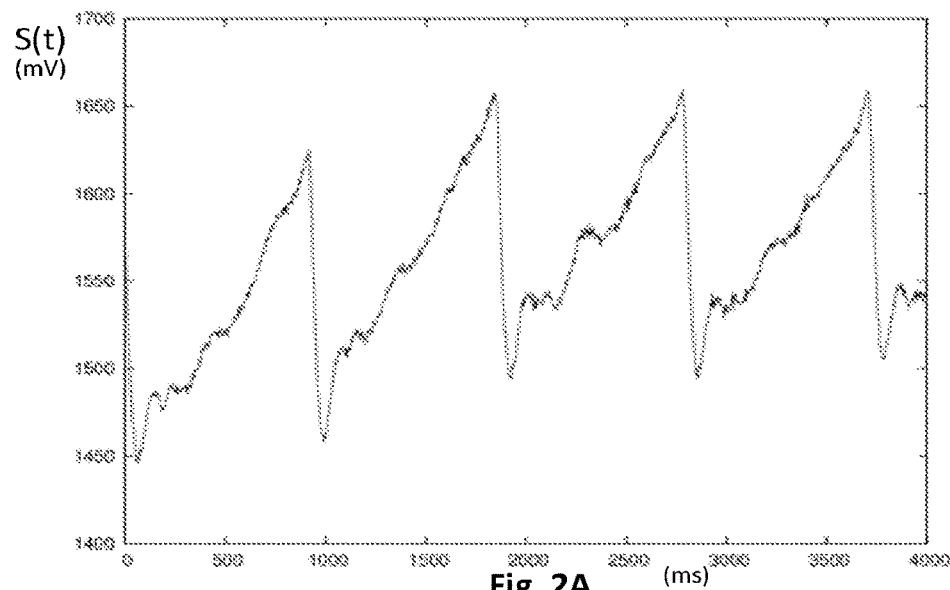
FIG. 2A shows a detection function obtained following detection of radiation backscattered by a bodily zone under the effect of an illumination.
Figure 2B:
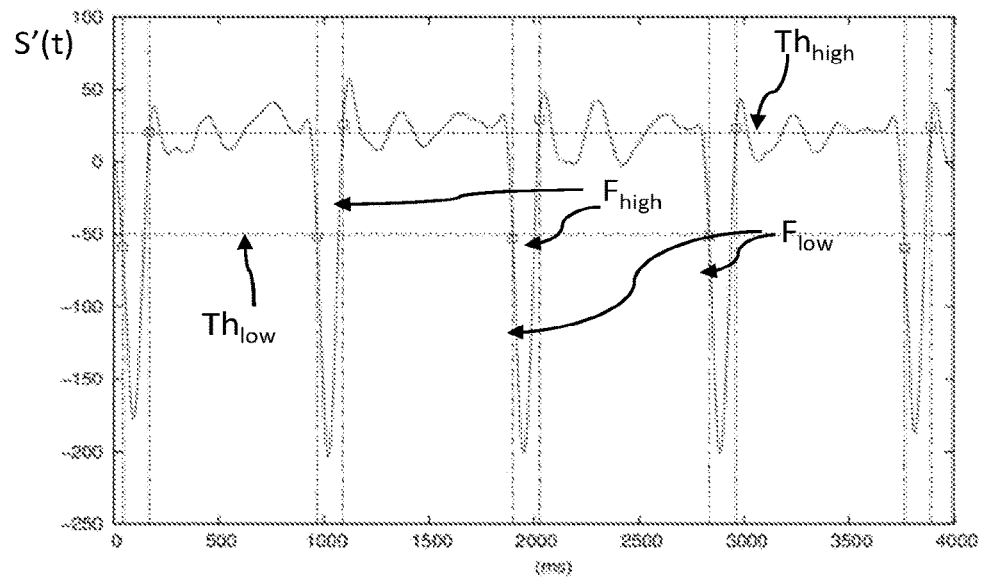
FIG. 2B shows what is called a derived function, obtained from a detection function such as shown in FIG. 2A.

FIG. 2A shows what is called a detection function S(t) representing the intensity, S, as a function of time, of backscattered (or transmitted) radiation detected by the photodetector 30, in the first spectral band. Under the effect of cardiac activity, the intensity of the backscattered radiation varies periodically as a function of time, the period of this variation depending on the cardiac frequency hr. FIG. 2B shows the variation, as a function of time, of what is called a derived function representing a time derivative of the detection function. It will be understood that it is easy to estimate the frequency of the function S'(t), the latter also corresponding to the frequency of the function S(t), which also corresponds to the sought cardiac frequency hr. A known prior-art method consists in using a low threshold $Th_{low}$ and a high threshold $Th_{high}$, so as to detect a descending front $F_{low}$ and a rising front $F_{high}$, respectively, in the derived function S'(t). The instants corresponding to a descending front, or to a rising front, are called characteristic instants. They are obtained by determining, to the nearest sampling period, the instant at which the derived function S'(t) crosses the low threshold $Th_{low}$ and the high threshold $Th_{high}$, respectively. The frequency f of the derived function is obtained by calculating a period between two successive characteristic instants, or an average of the time interval between a plurality of consecutive characteristic instants.

Figure 3A:
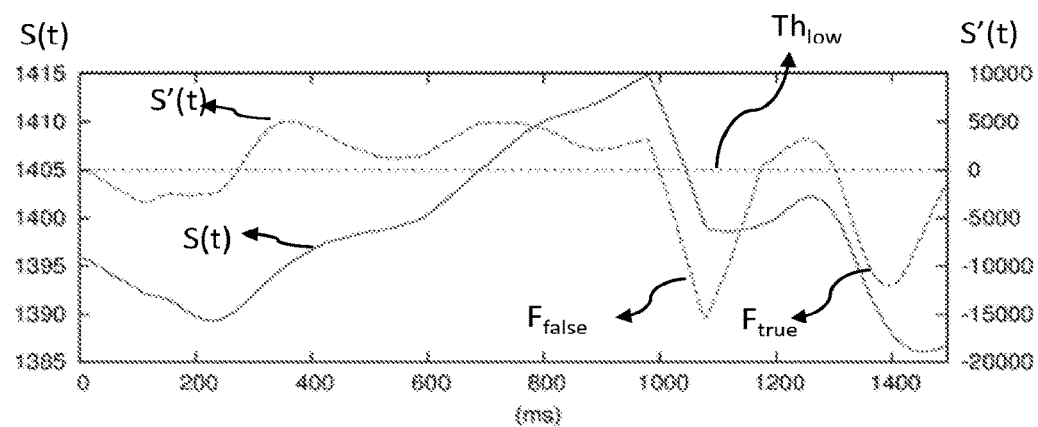
FIG. 3A shows a detail of a detection function, and its derived function, as a function of time. It illustrates the detection of a false front.

Such an estimation is generally calculated in a single spectral band, whether it be a red spectral band or an infrared spectral band. However, this type of estimation lacks robustness. More particularly, movements of the illuminated bodily zone, exposure to parasitic light sources or simple electronic noise may corrupt the estimation of cardiac frequency. FIG. 3A shows a detail of a detection function and of a derived function in a time interval of 1500 ms. This figure illustrates an example of detection of what is called a false descending front $F_{false}$ and what is called a true descending front $F_{true}$. The inventors have estimated that it is necessary to decrease the detection of false fronts, because their presence corrupts the estimation of cardiac frequency.

Figure 3B:
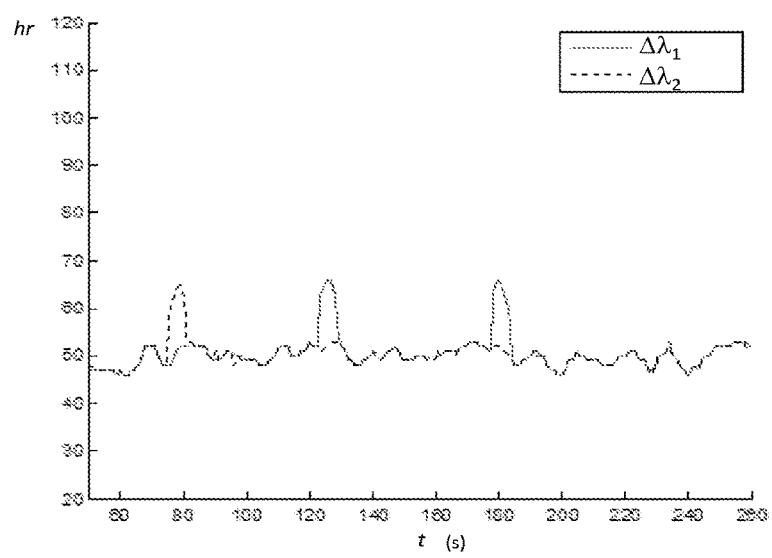
FIG. 3B shows, as a function of time, the cardiac frequency of an individual as estimated from a signal detected in response to an illumination in a spectral band centred on 660 nm and 940 nm, respectively. These estimations were calculated using a prior-art method and were obtained by illuminating the thumb of an individual, in a back-scatter configuration.

FIG. 3B shows estimations of cardiac frequency $hr_1$, $hr_2$, these estimations being calculated from a first detection function $S_1(t)$ obtained by illuminating a sample in the first spectral band $\Delta\lambda_1$, and a second detection function $S_2(t)$ obtained by illuminating the sample in the second spectral band $\Delta\lambda_2$, respectively. In each of these estimations, false variations in the estimations, due to the detection of false fronts such as the front $F_{false}$ described with reference to FIG. 3A, are observed.

Figure 4A:
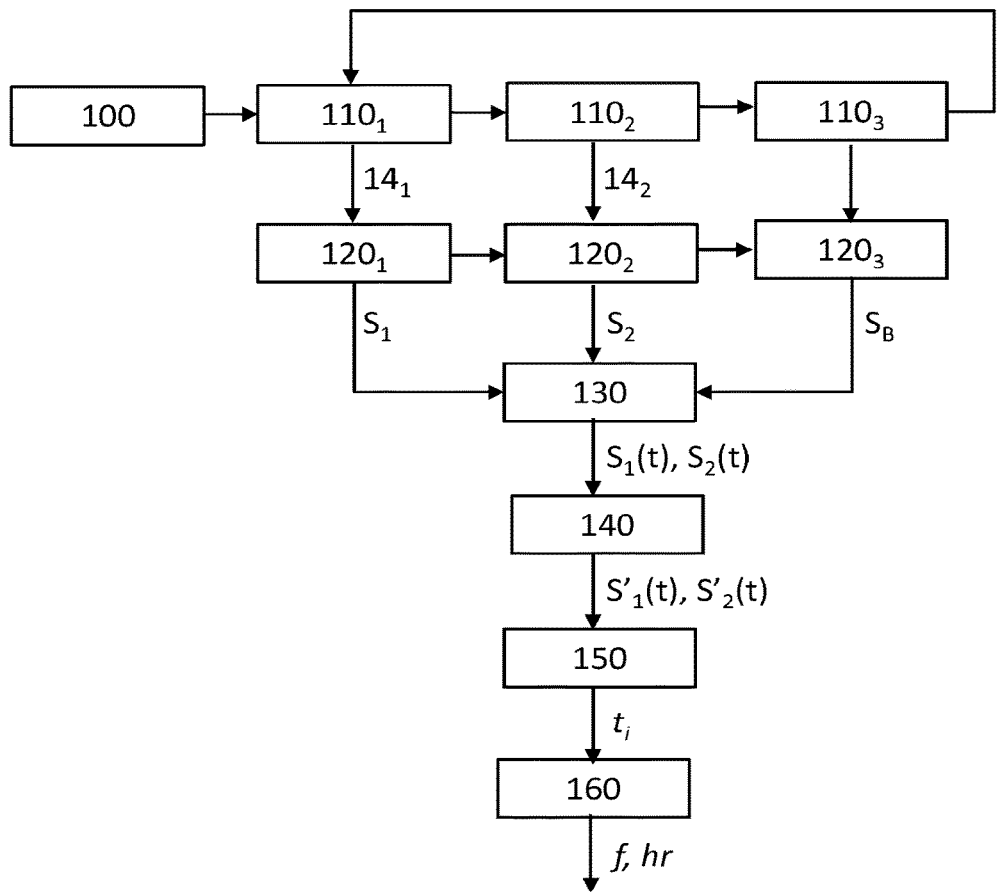
FIG. 4A shows the main steps of a method according to the invention.

The inventors have defined a method allowing the detection of false characteristic instants to be avoided. This method, which combines the detection of signals backscattered or transmitted in two spectral bands, will be described below with reference to FIG. 4A, the main steps of which are presented below.

Step 100: arranging the device 1 in such a way that the light source 10 is configured to illuminate a sample, i.e. a bodily zone 20 of a living being, and that the photodetector is configured to detect radiation backscattered or transmitted by the bodily zone consecutively to this illumination.

Step 110: illuminating the sample 20 in the first spectral band $\Delta\lambda_1$ (substep $110_1$) and in the second spectral band $\Delta\lambda_2$ (substep $110_2$). Depending on the photodetector used, this illumination may be simultaneous or successive. In this example, a single non-spectrally resolved photodetector is used. The sample is illuminated successively by each elementary source $10_1$ and $10_2$, the duration of each illumination being 1.66 ms. The successive activation of each elementary light source, which successive activation is designated by the term "illuminating sequence", is controlled by the microcontroller 15. Alternatively, the light sources may be continuously activated, the backscattered (or transmitted) radiation being detected by two different photodetectors, each being configured to detect the radiation in the first spectral band $\Delta\lambda_1$ or the second spectral band $\Delta\lambda_2$, respectively. According to another variant, the photodetector may be spectrally resolved, thereby also allowing the bodily zone 20 to be illuminated simultaneously in the two spectral bands. Preferably, but optionally, after the activation of the second light source, no light source is activated for 1.66 ms (substep $110_3$). The signal $S_B$ detected by the photodetector 30 is thus representative of a dark current of the latter.

Step 120: detecting radiation backscattered (or transmitted) by the sample following the illumination in each spectral band. The photodetector generates a first detection signal $S_1$ depending on the intensity of the radiation backscattered (or transmitted) $14_1$ under the effect of the illumination of the sample in the first spectral band $\Delta\lambda_1$ (substep $120_1$) and a second detection signal $S_2$ dependent on the intensity of the radiation backscattered (or transmitted) $14_2$ under the effect of the illumination of the sample in the second spectral band $\Delta\lambda_2$ (substep $120_2$). In this example, the first detection signal $S_1$ and the second detection signal $S_2$ are detected during the illumination by the first elementary source and during the illumination by the second elementary source, respectively. When no light source is activated, the photodetector acquires a background-noise signal or dark-current signal $S_B$ (substep $120_3$). This dark current may be subtracted from the detection signals $S_1$ and $S_2$.

Figure 4B:
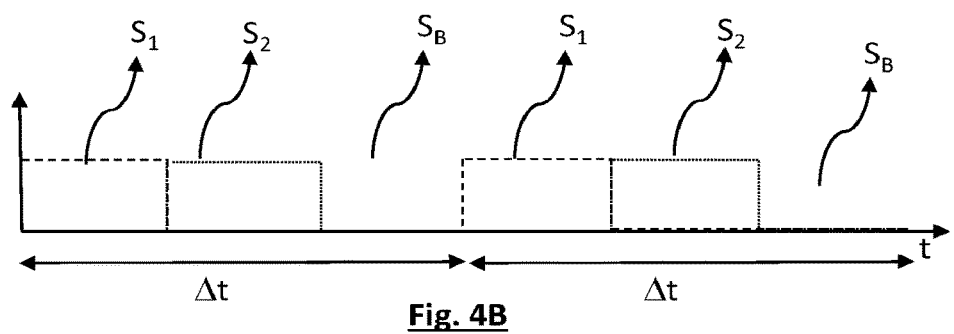
FIG. 4B illustrates each illuminating sequence of the method.

Thus, as shown in FIG. 4B, an illuminating sequence $\Delta t$ lasts 5 ms, and is subdivided into three time periods of 1.66 ms, respectively corresponding to:

the activation of the first elementary light source $10_1$, and the detection, by the photodetector, of a first signal $S_1$ representing the intensity of first radiation $14_1$ backscattered (or transmitted) by the sample;

the activation of the second elementary light source $10_2$, and the detection, by the photodetector, of a second signal $S_2$ representing the intensity of second radiation $14_2$ backscattered (or transmitted) by the sample;

the detection, by the photodetector, of a background-noise signal $S_B$ when no light source is activated.

Step 130: establishing a first detection function $S_1(t)$ and a second detection function $S_2(t)$ representing the variation as a function of time of the first detection signal $S_1$ and of the second detection signal $S_2$, respectively. Each of these functions is obtained by sampling over time the first signal $S_1$ and the second signal $S_2$, respectively, the sampling frequency for example being 200 Hz, this corresponding to an acquisition of a first signal $S_1$ and of a second signal $S_2$ every 5 ms. The establishment of each detection function may comprise a preprocessing step in which the signal is smoothed, allowing a high-frequency component of the detected signal to be removed. This preprocessing may take the form of application of a low-pass filter or of a moving average. In this example, a moving average is calculated for a time interval of 25 ms, i.e. 5 samples.

Step 140: determining a first derived function $S'_1(t)$ and a second derived function $S'_2(t)$. Each derived function is obtained via a difference of a detection function at two different times t and t+St. The time difference St is preferably smaller than 500 ms, or even than 100 ms. In this example, t and t+St are successive instants, i.e. instants spaced apart by the sampling period, i.e. 5 ms. The derived function may be obtained by normalizing the difference described above by the time difference, this corresponding to the conventional definition of a rate of variation.
In other words, $$S'_1(t) = S_1(t + \delta t) - S_1(t) \text{ or} \tag{1}$$

$$S'(t) = \frac{S_1(t + \partial t) - S_1(t)}{\partial t}. \tag{1'}$$

The second derived function $S'_2(t)$ is obtained identically to the first derived function $S'_1(t)$, from the second detection function $S_2(t)$.

Step 150: identifying characteristic instants. By characteristic instant, what is meant is an instant at which the detection function or its derived function reaches a particular value, crosses a threshold or reaches a local extremum, for example a local minimum or local maximum. In this example, as described with reference to FIGS. 2B and 3A, a characteristic instant corresponds to the instant at which a derived function crosses a threshold Th. Step 150 then includes a comparison of each value of each derived function to a threshold Th, so as to detect a descending front or a rising front. When the value of a derived function, for example the first derived function $S'_1$ (t), crosses such a threshold, a time window W is opened. The duration of this time window is short and for example comprised between 5 and 100 times the sampling period. It is preferably smaller than 500 ms and typically comprised between 20 ms and 200 ms. If, in this time window W, the other derived function, in the present case $S'_2(t)$, also crosses the threshold Th, the crossing of the threshold Th is validated for the two derived functions. The instant corresponding to the crossing of the threshold Th, by one of the two derived functions, is selected as being a characteristic instant $t_i$. The duration of the time window W may be preset or adjustable.

Figure 5A:
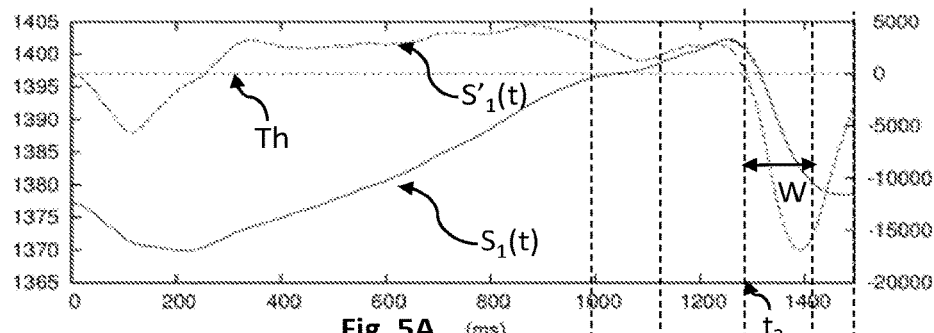
FIGS. 5A and 5B show characteristic instants detected using a first detection function and a second detection function, respectively.
Figure 5B:
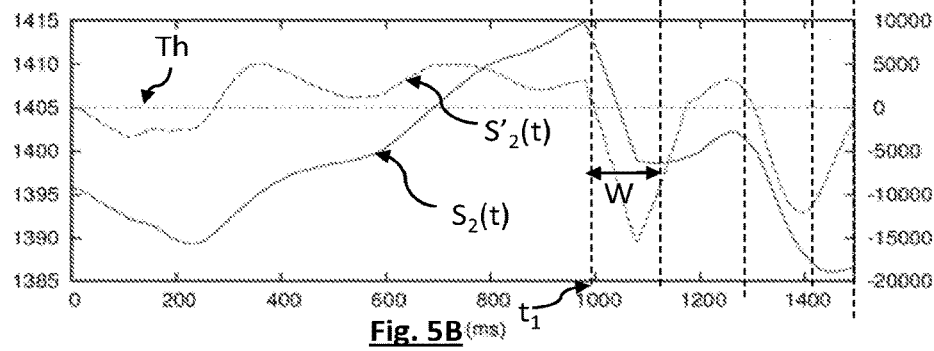

FIGS. 5A and 5B illustrate step 150. FIG. 5A shows a first detection function $S_1(t)$ and its derived function $S'_1(t)$. FIG. 5B shows a second detection function $S_2(t)$ and its derived function $S'_2(t)$. FIG. 5B is similar to FIG. 3A, which was described above. A first crossing of a threshold Th, by the second derived function $S'_2(t)$, is observed at $t=t_1$. When the threshold is crossed, a time window W of 100 ms duration is opened. During this time window, the first derived function $S'_1(t)$ is not detected to cross the threshold Th. The characteristic instant $t_1$ is therefore invalidated. A second crossing of the threshold Th by the first derived function $S'_1(t)$ is also observed at $t=t_2$. When the threshold is crossed, a new time window W is opened, during which a second crossing of the threshold is detected for the second derived function $S'_2(t)$. The two crossings of the threshold Th are then considered to have occurred, at the instant $t_2$, in temporal coincidence, or in other words simultaneously, to within a few sampling periods. The instant $t_2$ is therefore selected as being a characteristic instant $t_i$ to be considered for evaluation of cardiac frequency.

Step 160: determining cardiac frequency hr. From the characteristic instants $t_i$ selected in step 150, an occurrence frequency f of the successive characteristic instants is established, this frequency corresponding to the cardiac frequency hr. For example, the occurrence frequency is obtained by averaging the occurrence frequency of a number N of successive characteristic instants $t_i$. The frequency $f_i$ attributed to a characteristic instant $t_i$ may then be established depending on the average time difference between N successive instants preceding the characteristic instant, such that:

$$f_i = \frac{1}{\frac{1}{N-1} \sum_{j=i-N+2}^{j=i} (t_j - t_{j-1})} \tag{2}$$

The cardiac frequency $hr_i$ at the instant $t_i$ is equal to $f_i$. The units may then be changed to obtain a cardiac frequency in $\min^{-1}$.

Figure 6A:
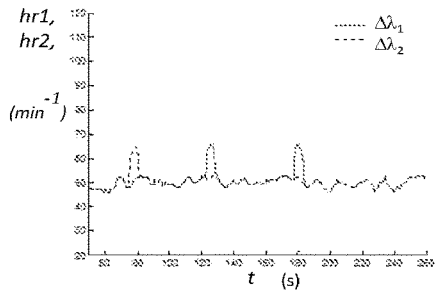
FIG. 6A is identical to FIG. 3B.
Figure 6B:
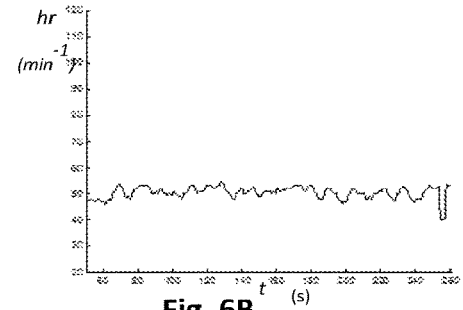
FIG. 6B shows the cardiac frequency of an individual as estimated, while implementing the invention, from the detected signals shown in FIG. 6A.

FIGS. 6A and 6B illustrate the advantage of the invention. These figures show an evaluation of the cardiac frequency of a man, the device being arranged in a back-scatter configuration, such as shown in FIG. 1A, on his thumb. FIG. 6A shows an estimation of the cardiac frequency according to the prior art, the measurements in the first spectral band and in the second spectral band being considered independently. FIG. 6B shows an estimation of the cardiac frequency from characteristic instants appearing in temporal coincidence, i.e. simultaneously, to within the width of the time window, in each spectral band. The detection functions used to establish FIGS. 6A and 6B were analogous. The cardiac frequency determined by implementing the invention is more stable. In particular, the parasitic fluctuations appearing, in FIG. 6A, at t=80 s, t=130 s and t=180 s, do not appear in FIG. 6B.

Figure 6C:
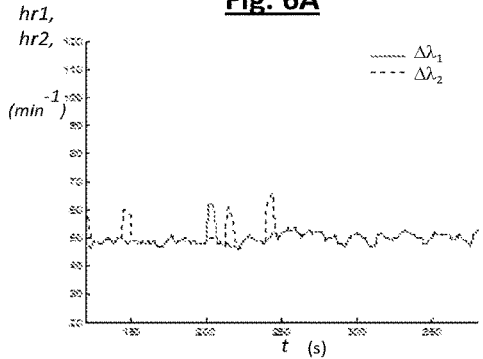
FIG. 6C corresponds to the cardiac frequency of an individual, estimated according to a prior-art method by illuminating the wrist of an individual.
Figure 6D:
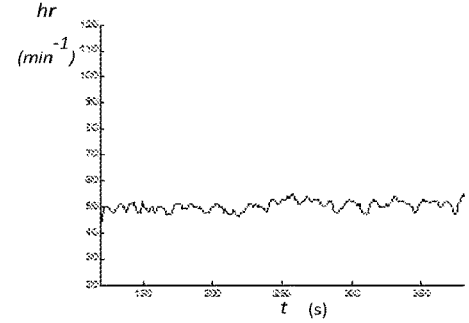
FIG. 6D corresponds to the cardiac frequency estimated, while implementing the invention, from the detected signal shown in FIG. 6C.

FIGS. 6C and 6D are analogous to FIGS. 6A and 6B, respectively, the device being placed level with the wrist of a man. An improvement in the precision of the estimation is also observed when the invention is applied.

The invention will possibly be implemented in devices to be worn by individuals and operating in a transmission or back-scatter mode. The back-scatter configuration is particularly suitable for integration into a compact watch-type device, a portable device for monitoring actigraphy or a dermal patch. In order to improve the reliability of the estimation, the device will preferably maintain contact with the skin of the person, or be kept a fixed distance from the latter, by means of a strap or another rigid or elastic mount structure.

The invention will possibly be used to monitor living beings, such as new-borns, elderly people, athletes or people at risk. The use of the red and infrared spectral bands are suitable for integration into pulsed oximetry devices based on the same spectral bands, so as to determine other physiological parameters, such as blood saturation, according to known methods.

The invention claimed is:

1. A Method for estimating a cardiac frequency of a living being including the following steps:
    a) illuminating a bodily zone of the living being with an incident light beam in a first spectral band;
    b) detecting light radiation transmitted or backscattered, in the first spectral band, by the bodily zone under the effect of the illumination;
    c) determining a first detection function, representing a variation as a function of time of an intensity of the light radiation thus detected;
    d) identifying characteristic instants from the first detection function, and calculating an occurrence frequency of the characteristic instants;
    e) estimating a cardiac frequency from the occurrence frequency calculated in step d);

wherein:
steps a) to b) are also implemented in a second spectral band, such that step c) includes determining a second detection function representing a variation as a function of time of an intensity of the light radiation detected in the second spectral band;

step d) includes identifying characteristic instants from the second detection function and selecting characteristic instants, identified from each detection function, and appearing in temporal coincidence, the occurrence frequency being calculated from the characteristic instants thus selected.

2. The method according to claim 1, wherein the second spectral band is different from the first spectral band.

3. The method according to claim 1, wherein step d) includes calculating a first derived function, derived from the first detection function, and a second derived function, derived from the second detection function, and identifying characteristic instants from each of the derived functions.

4. The method according to claim 3, wherein each derived function is obtained via a difference between the value of a detection function at two different instants.

5. The method according to claim 1 wherein:
the first spectral band includes wavelengths comprised between 600 and 700 nm;
the second spectral band includes wavelengths comprised between 750 nm and 1 μm.

6. The method according to claim 1, wherein the first spectral band extends between 600 nm and 700 nm, whereas the second spectral band extends between 750 nm and 1 μm.

7. The method according to claim 1, wherein the detected radiation is radiation backscattered by the bodily zone under the effect of its illumination.

8. A device for estimating a cardiac frequency of a living being, including:
a light source configured to emit an incident light beam that propagates towards a bodily zone of the living being, in a first spectral band and in a second spectral band;
a photodetector, configured to detect, in the first spectral band and in the second spectral band, radiation backscattered or transmitted by the bodily zone under the effect of its illumination by the incident light beam;
a processor, configured to process the radiations detected by the photodetector and to implement the steps c) to e) of the method according to claim 1.

9. The device according to claim 8, wherein the photodetector is configured to detect radiation backscattered by the bodily zone under the effect of its illumination.

10. The device according to claim 8, wherein the first spectral band is different from the second spectral band.

11. The device according to claim 8, wherein the light source includes:
a first elementary light source, configured to emit a first incident light beam in the first spectral band;
a second elementary light source, configured to emit a second incident light beam in the second spectral band.

* * * * *